US00PP33137P3

(12) United States Plant Patent
Mazzardis

(10) Patent No.: US PP33,137 P3
(45) Date of Patent: Jun. 8, 2021

(54) BLUEBERRY PLANT NAMED 'NS 16-8'

(50) Latin Name: ***Vaccinium* hybrid**
Varietal Denomination: NS 16-8

(71) Applicant: Next Progeny Pty., Ltd., Subiaco (AU)

(72) Inventor: Vincent David Andrew Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 16/991,921

(22) Filed: Aug. 12, 2020

(65) Prior Publication Data

US 2021/0051829 P1 Feb. 18, 2021

(30) Foreign Application Priority Data

Aug. 15, 2019 (QZ) ..... PBR 2019/1984

(51) Int. Cl.
*A01H 6/36* (2018.01)
*A01H 5/08* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Annette H Para
(74) *Attorney, Agent, or Firm* — Randall Danskin, P.S.

(57) ABSTRACT

A new and distinct variety of blueberry plant, which is denominated varietally as 'NS 16-8' is described, with a medium vigor and which produces fruit considered large in size and medium in firmness under the ecological conditions prevailing in Yanchep, Western Australia.

2 Drawing Sheets

CROSS REFERENCE TO RELATED APPLICATIONS

This application claims the benefit of priority under 35 USC § 119 to Community Plant Variety Office (CPVO) Application No. 2019/1984 for Community Plant Variety Rights, filed on Aug. 15, 2019 for a blueberry plant with a variety denomination of 'NS 16-8', which is herein incorporated by reference in its entirety.

Latin name: *Vaccinium* hybrid.

Variety denomination: The invention relates to a new, novel, and distinct variety of blueberry plant, a *Vaccinium* hybrid, with a variety denomination hereinafter as 'NS 16-8'.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, cross-pollinations were made in order to produce plant populations from which improved progeny were evaluated and thereafter selected.

The 'NS 16-8' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant 'EB 8-42' (U.S. Pat. No. 25,858), and a pollen parent, blueberry plant 'EB 9-2' (U.S. Pat. No. 28,149) during the 2013 growing season.

Prior Varieties. The seed parent 'EB 8-42' is characterized principally by a semi-upright growth habit, a medium to strong vigor, a very early season first pick date, and further produces large-sized, firm, medium to high sweetness, and low to medium acidity fruit under the ecological conditions occurring in Yanchep, Western Australia. Also, the seed parent 'EB 8-42' exhibits a very early date of bloom time, an August first pick date, and a December last pick date under the ecological conditions occurring in Yanchep, Western Australia. Further, the seed parent 'EB 8-42' is evergreen and produces fruit on one-year-old and current season's shoots.

The pollen parent 'EB 9-2', on the other hand, is characterized principally by an upright to semi-upright growth habit, a strong to very strong vigor, a very early season first pick date, and further produces large- to very-large-sized, firm to very firm, high sweetness, and low to medium acidity fruit under the ecological conditions occurring in Yanchep, Western Australia. Also, the pollen parent 'EB 9-2' exhibits a very early (February-March) date of bloom time, a March first pick date, and a December last pick date under the ecological conditions occurring in Yanchep, Western Australia. Further, the pollen parent 'EB 9-2' is evergreen and produces fruit on one-year-old and current season's shoots.

Origin. The seed from the seed parent 'EB 8-42' produced approximately 350 plants following cross-pollination. These new plants were then grown at the aforementioned property, and fruit from these new plants was first observed in 2015. A subsequent assessment of these same self-fertile, new plants conducted during the 2016 growing season and additionally during the 2017 growing season led to selecting the 'NS 16-8' variety for further evaluation.

Asexual Reproduction. The further evaluation included an asexual vegetative propagation, by vegetative cuttings, at Yanchep Springs in Yanchep, Western Australia. Subsequent evaluations of the newly derived plants in the 2018 growing season led to a conclusion that the 'NS 16-8' variety was a distinct and new variety of blueberry plant found to be true to the original plant. The new variety of blueberry plant was considered to be novel in view of its medium vigor and large fruit, which exhibited medium firmness.

Comparisons. In comparison to the seed parent 'EB 8-42' under the ecological conditions occurring in Yanchep, Western Australia, the new variety is noteworthy. In this regard, the seed parent exhibits a plant vigor considered to be medium to strong. However, the new variety of blueberry plant exhibits a plant vigor considered to be medium. In addition, the seed parent and the new variety of blueberry plant both produce fruit considered to be large in size. Further, the seed parent produces fruit considered to be firm. This is in contrast to the fruit of the new variety of blueberry plant, which is considered to be medium in firmness.

In comparison to the pollen parent 'EB 9-2' under the ecological conditions occurring in Yanchep, Western Australia, the new variety is noteworthy. In this regard, the pollen parent exhibits a plant vigor considered to be strong to very strong. However, the new variety of blueberry plant exhibits a plant vigor considered to be medium. In addition, the pollen parent produces fruit considered to be large to very large in size. In contrast, the fruit of the new variety of blueberry plant is considered to be large in size. Further, the pollen parent produces fruit considered to be firm to very firm. This is in contrast to the fruit of the new variety of blueberry plant, which is considered to be medium in firmness.

The new variety of blueberry plant is readily distinguishable from the most closely related, known variety, 'EB 9-2,' the pollen parent.

The comparisons described above are summarized in the table below.

Summary of Comparisons

| | 'NS 16-8' | 'EB 8-42' (Seed) | 'EB 9-2' (Pollen) |
|---|---|---|---|
| Plant vigor | Medium | Medium to strong | Strong to very strong |
| Fruit size | Large | Large | Large to very large |
| Fruit firmness | Medium | Firm | Firm to very firm |

BRIEF DESCRIPTION OF THE DRAWINGS

The accompanying drawings are color photographs of the new blueberry plant 'NS 16-8' during the second year of growth under the ecological conditions prevailing at the breeder's property, which is located at Yanchep Springs in Yanchep, Western Australia.

Figure 1:
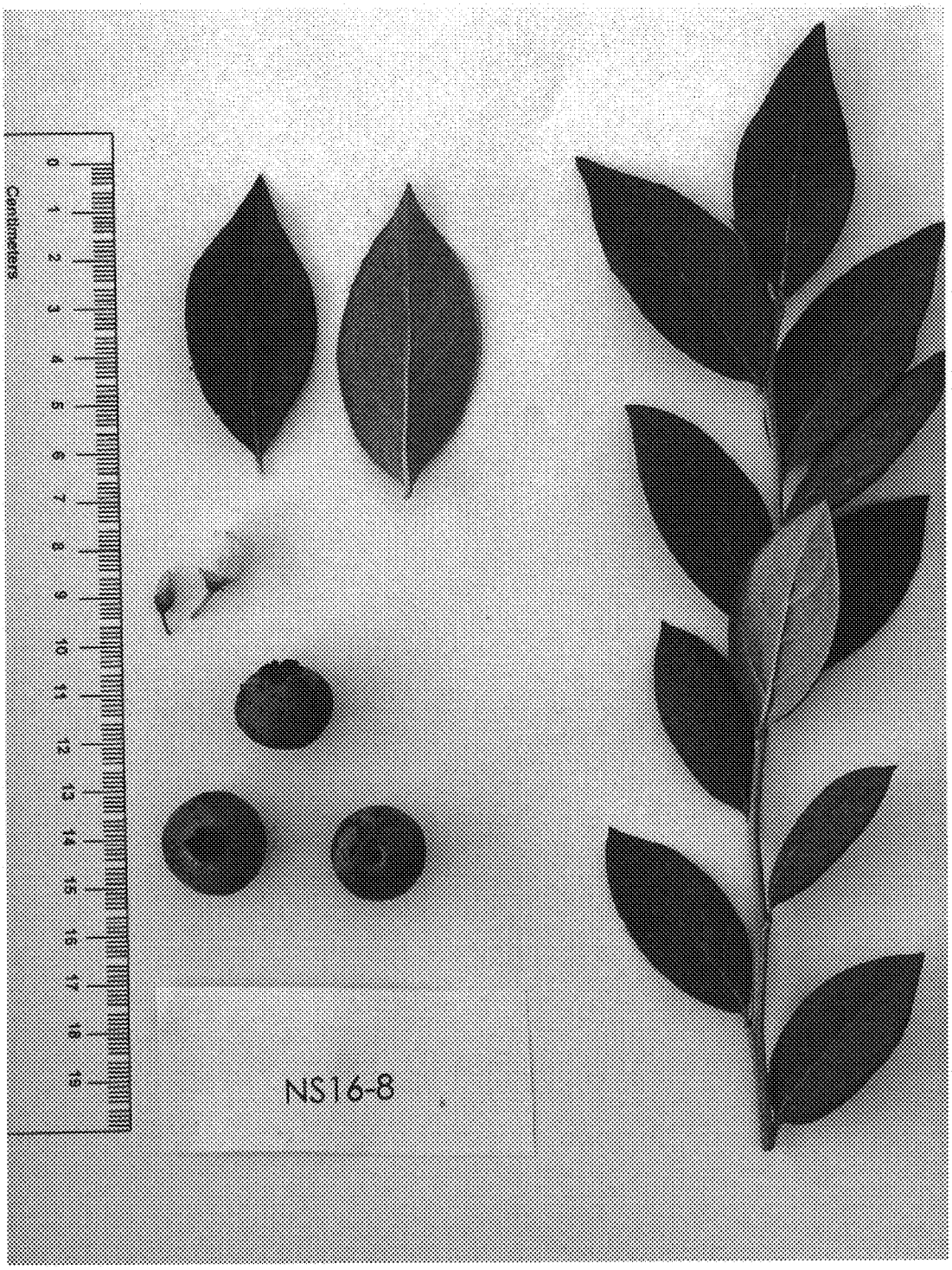
FIG. 1 is a color photograph, which shows fruit, blooms, leaves, and a portion of a vegetative stem of the new blueberry plant 'NS 16-8', the fruit being sufficiently mature for harvesting and shipment. This photograph also depicts the fruit size and the color of the ripe fruit, two leaves showing the sizes and the upper and under side colorations thereof, two blooms at different stages of maturation, and additional leaves on the stem at different stages of maturation.
Figure 2:
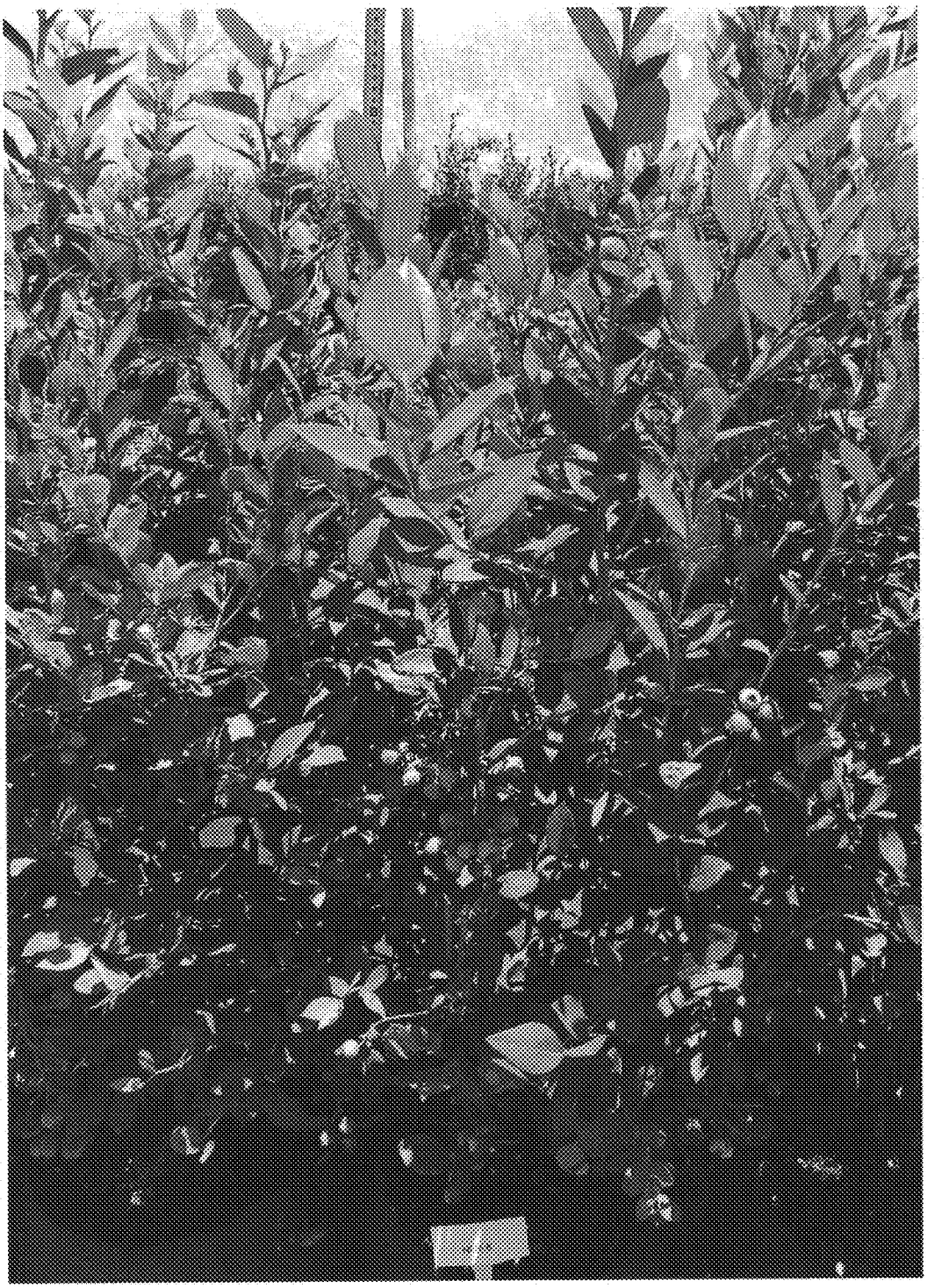
FIG. 2 is a color photograph, which shows the new blueberry plant 'NS 16-8.' This photograph depicts a mature bush with ripe and unripe fruits, the fruit size, and the upright growth habit of the bush. The ripe fruit is sufficiently mature for harvesting and shipment.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition, hereinafter, "RHS") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the second year of growth under the ecological conditions prevailing at the breeder's property, which is located at Yanchep Springs in Yanchep, Western Australia.

Plant: General.

*Vigor.*—Considered medium for the species. This is in contrast to the seed parent 'EB 8-42', wherein the vigor is considered medium to strong, and the pollen parent 'EB 9-2, wherein the vigor is considered strong to very strong.

*Growth habit.*—Considered upright. This is in comparison to the commercial variety 'Ivanhoe' (unpatented), which is considered to be upright.

*Average size of plant.*—1.2 meters in height by 0.55 meters in width.

*Internode length* (*space between nodes*).—Considered medium, 19.6 millimeters (mm).

*Bark color.*—RHS Moderate Reddish Brown Group 177A.

*Color, one year old shoots.*—RHS Strong Yellow Green Group 145A.

*Fruiting Type.*—On one-year-old shoot and current season shoots, in like manner to commercial varieties 'Concord' (unpatented) and 'Burlington' (unpatented).

Foliage: General.

*Average leaf length.*—Considered medium to long for the species, 61.2 mm.

*Average leaf width.*—Considered medium to broad for the species, 30.0 mm.

*Color of leaf upper.*—RHS Dark Yellowish Green Group 139A.

*Color of leaf underside.*—RHS Moderate Yellowish Green Group 148B.

*Vein color of plant leaf.*—RHS Greyish Yellow Green Group 148D.

*Venation pattern of leaf.*—Pinnate reticulate.

*Leaf apex texture.*—Glabrous.

*Leaf apex shape.*—Acute.
*Leaf base shape.*—Acute.
*Leaf shape.*—Elliptic.
*Leaf margin.*—Entire.
*Leaf arrangement of plant.*—Alternate.
*Petiole length.*—5.33 mm.
*Petiole diameter.*—1.99 mm.
*Petiole color.*—RHS Light Yellow Green Group 145C.

Flowers:
*Number of flowers/inflorescence.*—3-5.
*Length of inflorescence (excluding pedicel).*—Considered medium, 4.44 mm.
*Corolla shape.*—Urceolate.
*Corolla tube surface texture.*—Ridges are present on the corolla tube.
*Average corolla length.*—11.10 mm.
*Corolla diameter.*—8.06 mm.
*Corolla aperture size.*—4.95 mm.
*Corolla color.*—RHS White Group NN155B.
*Pedicel color.*—RHS Moderate Yellowish Green Group 139D.
*Pedicel length.*—8.37 mm.
*Average calyx diameter.*—Considered small to medium, 4.43 mm.
*Average calyx basin depth.*—Considered medium, 1.88 mm.
*Attitude of sepals.*—Erect.
*Type of sepals.*—Straight.

Reproductive organs:
*Size of pollen anthers.*—4.11 mm.
*Color of pollen anthers.*—RHS Brownish Orange Group 172C.
*Pistil length.*—9.36 mm.
*Pistil color.*—RHS Light Yellow Green Group 145B.

Fruit:
*Color of unripe fruit.*—RHS Light Yellow Green Group 145C.
*Color of fruit skin.*—RHS Bluish Black Group 203C, also considered "dark blue" in like color to the commercial variety 'Heerma' (unpatented), after removal of bloom.
*Color of ripe fruit flesh.*—RHS Strong Yellow Green Group 145A.
*Color of seeds.*—RHS Brownish Orange Group 167B.
*Average fruit size.*—19 mm in diameter and 20.74 mm in height, which is considered large for the species. This is comparable to the seed parent 'EB 8-42', which also produces fruit considered to be large. This is in contrast to the pollen parent 'EB 9-2', which produces fruit considered to be large to very large.
*Average weight of fruit.*—5.8 grams.
*Berry shape.*—Considered round.
*Sweetness when ripe.*—Considered medium for the species.
*Firmness when ripe.*—Considered medium for the species. This is in contrast to the seed parent 'EB 8-42', wherein the firmness is considered firm, and the pollen parent 'EB 9-2, wherein the firmness is considered firm to very firm.
*Acidity when ripe.*—Considered low to medium for the species.
*Cluster density.*—Considered medium dense for the species.
*Average fruit production.*—4 kilograms on a two-year-old bush.
*Storability of fruit.*—Considered excellent for the species.
*Market use of fruit.*—1st grade fresh market fruit.
*Date of bud burst.*—This variety is evergreen under the ecological conditions prevailing in Yanchep, Western Australia, but a bud break occurs the end of May, which is considered very early for the species.
*Date of bloom time.*—This variety is evergreen under the ecological conditions prevailing in Yanchep, Western Australia, but a bloom time occurs in mid July, which is considered very early on one-year old shoot in like manner to the commercial variety 'Patriot' (unpatented) and considered very early on current year's shoot before the commercial variety 'O'Neal' (unpatented), which is considered early.
*Duration of bloom time.*—8 weeks.
*Beginning of fruit ripening.*—Considered very early on one-year-old shoot in like manner to the commercial variety 'Bluetta' (unpatented) and considered very early on current year's shoot before the commercial variety 'O'Neal' (unpatented), which is considered early.
*First pick date.*—The observed date of the first pick is approximately September under the ecological conditions prevailing in Yanchep, Western Australia.
*Last pick date.*—The observed date of the last pick is approximately December under the ecological conditions prevailing in Yanchep, Western Australia.
*Pollination requirements.*—Self-fertile.
*Resistance to pests and disease.*—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a plant letters patent is:

1. A new and distinct variety of blueberry plant, substantially as illustrated and described, which is characterized principally as to novelty by a medium vigor and by producing fruit considered large in size and medium in firmness under the ecological conditions prevailing in Yanchep, Western Australia.

* * * * *